(12) United States Patent
Biftu et al.

(10) Patent No.: US 7,429,590 B2
(45) Date of Patent: Sep. 30, 2008

(54) ANTIPROTOZOAL IMIDAZOPYRIDINE COMPOUNDS

(75) Inventors: Tesfaye Biftu, Westfield, NJ (US); Matthew J. Wyvratt, Mountainside, NJ (US); Michael H. Fisher, deceased, late of Ringoes NJ (US); by Louis L. Zuegner, III, legal representative, Flemington, NJ (US)

(73) Assignee: Merck & Co. Inc., Rahway, NJ (US)

( * ) Notice: Subject to any disclaimer, the term of this patent is extended or adjusted under 35 U.S.C. 154(b) by 254 days.

(21) Appl. No.: 10/573,363

(22) PCT Filed: Dec. 6, 2004

(86) PCT No.: PCT/US2004/040617

§ 371 (c)(1),
(2), (4) Date: Mar. 24, 2006

(87) PCT Pub. No.: WO2005/060571

PCT Pub. Date: Jul. 7, 2005

(65) Prior Publication Data
US 2006/0293303 A1 Dec. 28, 2006

Related U.S. Application Data

(60) Provisional application No. 60/528,570, filed on Dec. 10, 2003.

(51) Int. Cl.
C07D 401/04 (2006.01)
C07D 403/04 (2006.01)
C07D 417/04 (2006.01)
A61K 31/4188 (2006.01)

(52) U.S. Cl. .................. 514/241; 514/242; 514/252.04; 514/256; 514/300; 544/180; 544/182; 544/238; 544/333

(58) Field of Classification Search .................. 544/180, 544/182, 238, 333; 546/121; 514/241, 242, 514/252.04, 256, 300
See application file for complete search history.

(56) References Cited

U.S. PATENT DOCUMENTS 6,596,731 B2    7/2003    Mutel et al.

Primary Examiner—Deepak Rao
(74) Attorney, Agent, or Firm—Sylvia A. Ayler; William Krovatin

(57) ABSTRACT

Compounds described by the Formula (I) or (II): or pharmaceutically acceptable salts, or N-oxides thereof. The compounds are useful for the treatment and prevention of protozoal diseases in mammals and birds. A method for controlling coccidiosis in poultry comprises administering an effective amount of the compound alone, or in combination with one or more anticoccidieal agent(s). A composition for controlling coccidiosis in poultry comprises the compound alone, or in combination with one or more anticoccidial agent(s). Methods for the treatment and prevention of mammalian protozoal diseases, such as, for example, toxoplasmosis, malaria. African typanosomiasis, Chagas disease, and opportunistic infections comprise administering the compound alone, or in combination with one or more antiprotozoal agent(s).

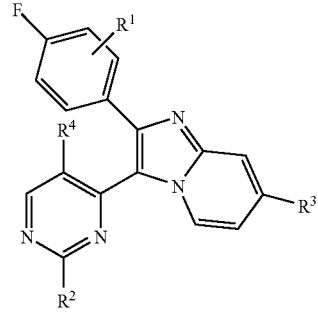

(I)

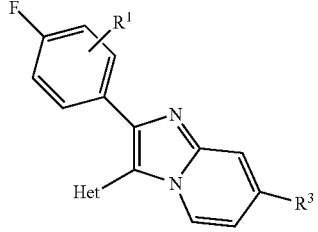

(II)

46 Claims, No Drawings

ANTIPROTOZOAL IMIDAZOPYRIDINE COMPOUNDS

RELATED APPLICATION DATA

This is a National filing under 35 USC 371 of PCT/US2004/040617, filed Dec. 6, 2004, which claims priority from U.S. Ser. No. 60/528,570, filed Dec. 10, 2003.

FIELD OF THE INVENTION

The present invention relates to imidazopyridines useful for the treatment and prevention of protozoal diseases in mammals and birds. In particular, this invention relates to trisubstituted imidazopyridines useful for the treatment and prevention of coccidiosis in poultry. The compounds of the instant invention are also useful for the treatment and prevention of mammalian protozoal diseases, including toxoplasmosis, malaria, African trypanosomiasis, Chagas disease and opportunistic infections.

BACKGROUND OF THE INVENTION

Parasitic protozoa are responsible for a wide variety of infections in both humans and animals. Protozoans of the genus *Eimeria* cause coccidiosis, a widespread disease of domesticated animals that causes severe pathology in the intestines and ceca. The most pathological species in this genus include *E. tenella, E. acervulinia, E. mitis, E. necatrix, E. brunetti* and *E. maxima*. Animal coccidiosis is generally spread by animals picking up the infectious organism from droppings on contaminated litter or the ground, or from food or drinking water. Coccidiosis is manifested by hemorrhage, accumulation of blood in the ceca, passage of blood in the droppings, weakness and digestive disturbances. The disease often terminates in the death of the animal, while those that survive severe coccidiosis infection have had their market value substantially reduced as a result of such infections. Coccidiosis is, therefore, a disease of great economic importance. Accordingly, extensive work has been done to find new and improved methods for controlling and treating coccidial infections in animals.

In the poultry industry, it is common practice to include anticoccidial agents in poultry feed for most of the bird's life to control or prevent coccidiosis outbreaks. However, there is a risk that the causative organisms will develop resistance after continuous or repeated exposure-to-any particular anticoccidial agent. Furthermore, conventionally used anticoccidial agents such as sulfanilamides, nitrofurans, quinolines, antithiamines, benzoamides, and polyether-based antibiotics are often toxic to the hosts. Therefore, there is a continuing need to identify new anticoccidial compounds, preferably in a different chemical class from currently used agents.

Parasitic protozoa are also responsible for a variety of human diseases, many of which are life threatening. Malaria remains a significant health threat to humans despite massive international attempts to eradicate the disease. Another parasitic disease, trypanosomiasis, poses health risks to millions of people across multiple countries in Africa and North and South America Visitors to these regions, such as business travelers and tourists, are also at risk for contracting parasitic diseases. There are two types of African trypanosomiasis, also known as sleeping sickness. One type is caused by the parasite *Trypanosoma brucei gambiense*, and the other is caused by the parasite *Trypanosoma brucei rhodesiensi*. If left untreated, African sleeping sickness results in death. Chagas disease, caused by *Trypanosoma cruzi*, affects millions of people in Mexico and South and Central America. Untreated Chagas disease causes decreased life expectancy and can also result in death. There are currently no satisfactory treatments available for these diseases. Currently available treatments are not entirely effective, and can even be toxic to the patient. For some diseases, drug-resistant strains of the protozoa can develop. A need thus exists for an antiparasitic compound for humans that is more effective and less toxic than those currently available.

The risk of parasitic diseases is also present outside developing countries. Opportunistic infections in immunocompromised hosts caused by *Pneumocystis carinii, Toxoplasma gondii*, and *Cryptosporidium* sp. are becoming increasingly prevalent in developed countries. For example, toxoplasmosis, which is caused by the parasite *Toxoplasma gondii*, is found in countries throughout the world, including the United States. Pregnant women and those with weak immune systems are particularly susceptible to health risks resulting from *Toxoplasma* infection. Severe toxoplasmosis can result in damage to the brain, eyes, and other organs. Currently available treatments for toxoplasmosis, which include the drugs trisulfa-pyrimdine, sulfadiazine and pyrimethamine, are not effective, and can be toxic to the host. Therefore, there is a need for therapeutic agents to treat toxoplasmosis that are more effective and less toxic than currently available treatment agents.

PCT Published Application WO03/000682 discloses compounds of the formula:

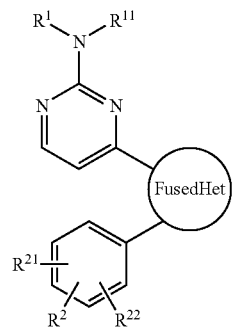

PCT Published Application WO03/000689 discloses compounds of the formula:

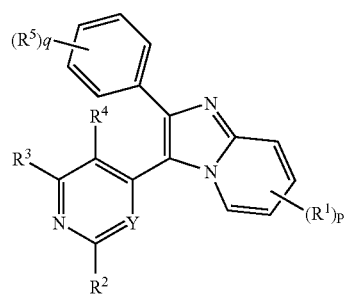

SUMMARY OF THE INVENTION

The present invention is directed to trisubstituted imidazopyridines that are useful for the treatment and prevention of protozoal diseases in mammals and birds. The present invention is also directed to compositions comprising such compounds, either alone or in combination with one or more antiprotozoal agents. The present invention further provides methods of using the instant compounds, either alone, or together with one or more anticoccidial agents, to prevent and treat coccidiosis in poultry. The compounds of the present invention are also useful for the prevention and treatment of protozoal diseases in mammals, including toxoplasmosis, malaria, African trypanosomiasis, Chagas disease, and opportunistic infections.

DETAILED DESCRIPTION OF THE INVENTION

The present invention provides compounds of Formula (I):

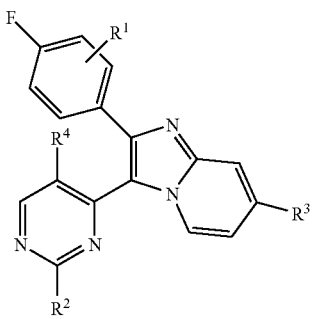

(I)

or pharmaceutically acceptable salts, or N-oxides, thereof, wherein $R^1$ is
  (a) hydrogen,
  (b) $C_1$-$C_6$-alkyl,
  (c) halogen;

$R^2$ is
  (a) hydrogen,
  (b) $C_1$-$C_6$-alkyl, optionally substituted with one or more of halogen, —OH, or aryl,
  (c) cycloalkyl,
  (d) $CF_3$,
  (e) aryl, optionally substituted with one or more of halogen or alkyl,
  (f) heteroaryl, optionally substituted with one or more of alkyl or halogen;

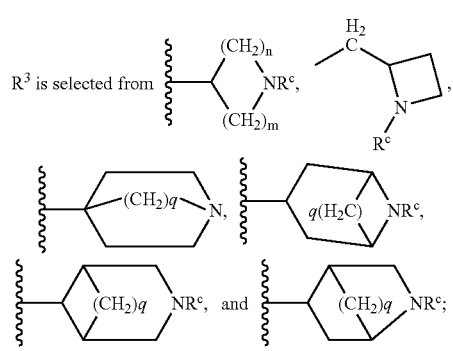

$R^c$ is selected from hydrogen and $C_{1-4}$alkyl, wherein alkyl is optionally substituted with one or more of halogen or —OH;
n and m are independently 0, 1, 2, 3 or 4, provided that n+m=2, 3 or 4;

q is 1 or 2; and
$R^4$ is hydrogen or halogen.

The present invention further comprises compounds represented by Formula (II)

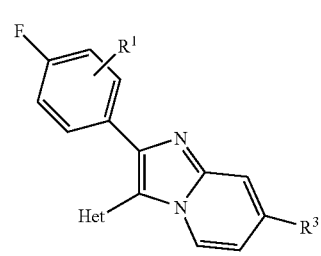

(II)

or pharmaceutically acceptable salts, or N-oxides, thereof, wherein

Het is heteroaryl, optionally substituted with one or more of amino, alkyl or halogen; and $R^1$ and $R^3$ each is as defined above.

In a first aspect, the present invention provides a compound described by the chemical Formula (I), or a pharmaceutically acceptable salt, or an N-oxide thereof, wherein $R^2$ is optionally substituted $C_1$-$C_6$-alkyl.

In a second aspect, the present invention provides a compound described by chemical Formula (I), or a pharmaceutically acceptable salt, or an N-oxide thereof, wherein $R^2$ is cycloalkyl.

In a third aspect, the present invention provides a compound described by the chemical Formula (I), or a pharmaceutically acceptable salt, or an N-oxide thereof, wherein $R^2$ is $CF_3$.

In a fourth aspect, the present invention provides a compound described by the chemical Formula (I), or a pharmaceutically acceptable salt, or an N-oxide thereof, wherein $R^2$ is optionally substituted aryl.

In a fifth aspect, the present invention provides a compound described by the chemical Formula (I), or a pharmaceutically acceptable salt, or an N-oxide thereof, wherein $R^2$ is optionally substituted heteroaryl.

In a sixth aspect, the present invention provides a compound described by the chemical Formula (I), or a pharmaceutically acceptable salt, or an N-oxide thereof, wherein

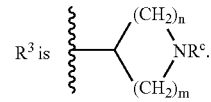

In a seventh aspect, the present invention provides a compound described by the chemical Formula (I), or a pharmaceutically acceptable salt, or an N-oxide thereof, wherein

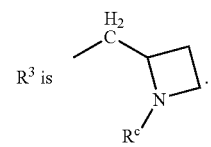

In an eighth aspect, the present invention provides a compound described by the chemical Formula (I), or a pharmaceutically acceptable salt, or an N-oxide thereof, wherein

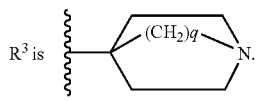

In a ninth aspect, the present invention provides a compound described by the chemical Formula (I), or a pharmaceutically acceptable salt, or an N-oxide thereof, wherein

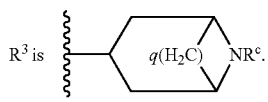

In a tenth aspect, the present invention provides a compound described by the chemical Formula (I), or a pharmaceutically acceptable salt, or an N-oxide thereof, wherein

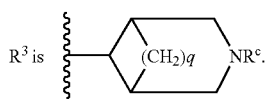

In an eleventh aspect, the present invention provides a compound described by the chemical Formula (I), or a pharmaceutically acceptable salt, or an N-oxide thereof, wherein

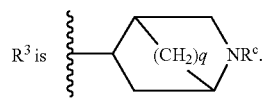

In a twelfth aspect, the present invention provides a compound described by the chemical Formula (I), or a pharmaceutically acceptable salt, or an N-oxide thereof, wherein
$R^3$ is piperidinyl.

In a thirteenth aspect, the present invention provides a compound described by the chemical Formula (I), or a pharmaceutically acceptable salt, or an N-oxide thereof, wherein
$R^3$ is [($C_{1-4}$)alkyl]piperidinyl.

In a fourteenth aspect, the present invention provides a compound described by the chemical Formula (I), or a pharmaceutically acceptable salt, or an N-oxide thereof, wherein
$R^3$ is 1-methylpiperidinyl.

In a fifteenth aspect, the present invention provides a compound described by the chemical Formula (I), or a pharmaceutically acceptable salt, or an N-oxide thereof, wherein
$R^3$ is 1-methylpiperidin-4-yl.

In a sixteenth aspect, the present invention provides a compound described by the chemical Formula (I), or a pharmaceutically acceptable salt, or an N-oxide thereof, wherein
$R^3$ is piperidin-4-yl.

In a seventeenth aspect, the present invention provides a compound described by the chemical Formula (I), or a pharmaceutically acceptable salt, or an N-oxide thereof, wherein
$R^3$ is [($C_{1-4}$) alkyl]piperidin-4-yl.

In an eighteenth aspect, the present invention provides a compound described by the chemical Formula (I), or a pharmaceutically acceptable salt, or an N-oxide thereof, wherein
$R^3$ is 1-(3-hydroxypropyl)-4-piperidinyl.

In a nineteenth aspect, the present invention provides a compound described by the chemical Formula (I), or a pharmaceutically acceptable salt, or an N-oxide thereof, wherein
$R^3$ is 1-(3-hydroxyethyl)-4-piperidinyl.

In a twentieth aspect, the present invention provides a compound described by the chemical Formula (II), or a pharmaceutically acceptable salt, or an N-oxide thereof, wherein
Het is pyridyl.

In a twenty-first aspect, the present invention provides a compound described by the chemical Formula (II), or a pharmaceutically acceptable salt, or an N-oxide thereof, wherein
Het is pyridazinyl.

In a twenty-second aspect, the present invention provides a compound described by the chemical Formula (II), or a pharmaceutically acceptable salt, or an N-oxide thereof, wherein
Het is triazinyl.

In a twenty-third aspect, the present invention provides a compound described by the chemical Formula (II), or a pharmaceutically acceptable salt, or an N-oxide thereof, wherein
Het is thiazolyl.

In a twenty-fourth aspect, the present invention provides a compound described by the chemical Formula (II), or a pharmaceutically acceptable salt, or an N-oxide thereof, wherein
Het is isothiazolyl.

Compounds of Formula (I) and (II) are useful in the prevention and treatment of protozoal diseases in birds, including the prevention and treatment of coccidiosis in poultry. The instant compounds are also useful for the prevention and treatment of mammalian protozoal diseases, including toxoplasmosis, malaria, African trypanosomiasis, Chagas disease, and opportunistic infections.

The invention relates to compositions comprising a compound of Formula (I) or (II) alone, or in combination with one or more antiprotozoal or anticoccidial agents.

The present invention includes methods of treating and preventing coccidiosis in poultry comprising administering a prophylactically effective amount, or a therapeutically effective amount, of a compound of Formula (I) or (II) alone, or in combination with one or more anticoccidial agents.

The present invention also includes methods of treating and preventing protozoal diseases in mammals comprising administering a prophylactically effective amount, or a therapeutically effective amount, of a compound of Formula (I) or (II) alone, or in combination with one or more antiprotozoal agents.

Unless otherwise stated or indicated, the following definitions shall apply throughout the specification and claims.

The term "pharmaceutically acceptable carrier" means generally safe and tolerated by the host species being treated.

The term "prophylactically effective amount" means an amount effective to prevent a disease, illness or sickness.

The term "therapeutically effective amount" means an amount effective to treat, cure or ameliorate a disease, illness or sickness.

It will be understood that, as used herein, references to the compounds of the present invention are meant to also include its N-oxides and salts. The tertiary amines of the instant compounds are capable of forming N-oxides such as, for example, the following:

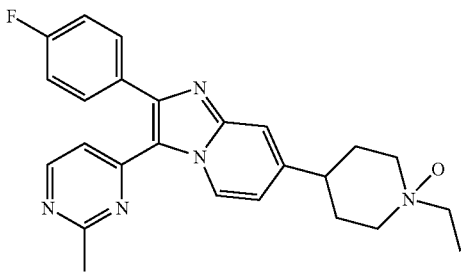

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The term "composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention, either alone, or together with one or more antiprotozoal or anticoccidial agents, and a pharmaceutically acceptable carrier.

Compositions of the present invention may be prepared in accordance with any conventional method known in the art. Thus, compositions of the present invention for controlling coccidiosis can be formulated into spreads, granules, suspensions, solutions, premixes, capsules, emulsions concentrates, tablets, feedstuff and so forth. Compositions of the present invention can contain the inventive compound either as a single substance or with or without suitable carriers that are ordinarily used for such medicaments. An excipient, such as a disintegrating agent, sliding agent, or coating agent, can be added to the instant compositions as needed in accordance with methods known in the art. The carriers usable in the instant compositions for controlling coccidiosis are not limited so long as they can be added to livestock feed or drinking water. Examples of suitable carriers include water, milk sugar, cane sugar, talc, colloidal silica, pectin, wheat flour, rice bran, corn flour, soybean, oil cake, ground or powdered grain, and other commercial livestock feeds. Although there are no specific limitations to the content or concentration of the active component, the preferable content is from about 0.1 to about 99% by weight, more preferably, from about 0.1 to about 50% by weight.

As used herein, the term "alkyl" as well as other terms having the prefix "alk" such as, for example, alkoxy, alkanoyl, alkenyl, alknyl and the like, includes carbon chains which may be linear or branched or combinations thereof. Examples of alkyl groups include methyl, ethyl, propyl, isopropyl, butyl, sec- and tert-butyl, pentyl, ispentyl, hexyl, isohexyl, heptyl and the like.

The term "aryl" as used herein includes an aromatic carbocycle having from 6 to 10 carbon atoms, optionally fused to a $C_4$-$C_6$ non-aromatic ring optionally containing 1-3 heteroatoms selected from N, O and S. Examples of aryl groups include phenyl and naphthyl.

The term "cycloalkyl" as used herein includes carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" includes carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "halogen" as used herein includes fluorine, chlorine, bromine and iodine.

The term "heteroaryl" as used herein includes a mono-or bicyclic aromatic ring containing from 1 to 6 heteroatoms independently selected from N, O and S wherein each ring has five or six ring atoms. Examples of heteroaryl include pyridyl, pyrimidinyl, pyridazinyl, pyrrolyl, furyl, thienyl, imidazolyl, thiazolyl, isothiazolyl, thiadiazolyl, thiophene, triazinyl, triazolyl, tetrazolyl, oxadiazolyl, oxazolyl, imidazolidinyl, pyrazolyl, isoxazolyl, benzothiadiazolyl, indolyl, indolinyl, benzodioxolyl, benzodioxanyl, benzothiophenyl, benzofuranyl, benzimidazolyl, benzisoxazolyl, benzothiazolyl, quinolinyl, benzotriazolyl, benzoxazolyl, purinyl, furopyridine and thienopyridine.

The term "heterocycle" or "heterocycloalkyl" as used herein includes a 3- to 7-membered non-aromatic ring containing 14 heteroatoms selected from N, O and S, which may be optionally fused to a benzene ring. Examples of heterocycle and heterocycloalkyl include oxiranyl, aziridinyl, azetidinyl, oxetanyl, tetrahydrofuranyl, tetrahydropyranyl, pyrrolidinyl, imidazolyl, imidazolidinyl, piperidinyl, morpholinyl, thiomorpholinyl, piperazinyl, benzoxazinyl, 2,3-dihydrobenzofuranyl 1,2,3,4-tetrahydroisoquinolinyl, and 1,2,3,4-tetrahydro-quinolinyl.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the alkyl and the aryl groups are optionally substituted. If only one of the multiple moieties is optionally substituted then it will be specifically recited such as "an alkylaryl, the aryl optionally substituted with halogen or hydroxyl."

Compounds described herein may contain one or more double bonds and may thus give rise to cis/trans isomers as well as other conformational isomers. The present invention includes all such possible isomers as well as mixtures of such isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed within compounds of Formula (I) and (II).

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formulas (I) and (II) are shown without a definitive stereochemistry at certain positions. The present invention includes all stereoisomers of Formula (I) and (II) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The compounds of the present invention may have chiral centers other than those centers whose stereochemistry is depicted in Formula (I) and (II), and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

Compounds of the present invention can be employed for the control of coccidiosis in any species. The terms "control of coccidiosis" and "controlling coccidiosis" include prophylactic use to prevent coccidiosis as well as use to treat coccidiosis after infection has occurred. Compounds of the present invention can be used for the control of coccidiosis in any poultry species, including, but not limited to, chicken, turkeys, ducks, geese, quail, pheasants, emus and ostriches. Compounds of the present invention can also be used for the control of coccidiosis in any other species, such as, for example, cattle, canines, sheep, horses, goats, and swine. Compounds of the present invention can be used to prevent or treat coccidiosis caused by any species of the causative protozoa, including *Eimeria acervulina, Eimeria brunetti, Eimeria maxima, Eimeria mitis, Eimeria necatrix, Eimeria tentella, Eimeria meleagrimitis, Eimeria gallopavonis, Eimeria adenoeides, Eimeria dispersa.*

Because coccidiosis is an intestinal malady, compounds of the present invention must be administered in a way that will allow them to reach the intestinal tract. Compounds of the instant invention can be administered according to standard methods known in the art, including by incorporating them into animal feed. The present compound can also be administered by other methods, such as by incorporating it into drinking water. In the most preferred practice, the present compound is administered in the feed.

Of the various methods of administering the compounds of this invention to poultry, the most convenient involves administering them as a component of a feed composition. The novel compound may be readily dispersed throughout feedstuff by mechanically mixing the compound in finely ground form with the poultry feedstuff, or with an intermediate formulation (premix) that is subsequently blended with other components to prepare the final poultry feedstuff. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

When the compound according to the present invention is used as an additive to poultry feed, it is typically incorporated into a "premix." The premix contains the active agent or agents as well as pharmaceutically acceptable carriers and feedstuffs. The premix is relatively concentrated and is adapted to be diluted with other carriers, vitamin, mineral supplements, and feedstuffs to form the final animal feed. Premixes that contain an intermediate concentration of active agent, that is, a concentration between that of the first premix and the final animal feed, are sometimes employed in the industry and can be used in implementing the present invention. When employing the present compound as a sole active agent, a premix desirably contains the agent at a concentration of from about 0.1 to about 50.0% by weight. Preferred premixes will generally contain the present compound at a concentration of from about 0.5 to about 25.0%, by weight. In final feeds, the concentration of the active agent will depend on various factors known to those skilled in the art. Such factors include the relative potency of the particular active agent and the severity of the actual or potential coccidial infection. In general, a final feed employing a compound of the present invention as the sole anticoccidial will contain from about 0.002 to about 0.02% by weight of said compound, preferably from about 0.002 to about 0.01%.

The present invention contemplates using a compound of Formula (I) or (II) as the sole anticoccidial agent as well as in combination with one or more anticoccidial agents. Suitable anticoccidials for such combination use include, but are not limited to, amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril. When used in combination with one or more anticoccidial agents, the compound of Formula (I) or (II) may be administered at or lower than the effective dosage levels used for the instant compound when it is adminstered alone; for example, the final feed may contain from about 0.0001 to about 0.02% by weight, or preferably from about 0.0005 to about 0.005% of a compound of Formula (I) or (II). Similarly, the additional anticoccidial agent(s) in the combination may be used in an amount at or lower than that commonly used for the instant compound when it is administered alone. Compositions comprising a compound of Formula (I) or (II) and one or more anticoccidial agents may be formulated into medicaments for preventing or treating coccidiosis in poultry and other species as described previously.

Compositions of the instant invention can contain, in addition to anticoccidial agent(s), therapeutic or nutritional agents commonly administered to poultry in the feed or drinking water, such as, for example, parasiticides, antibacterials, and growth promoters.

The compounds of Formula (I) and (II) are also useful for treating parasitic diseases in mammals. These diseases include toxoplasmosis, malaria, African trypanosomiasis, Chagas disease and opportunistic infections. The terms "control of toxoplasmosis" and "controlling toxoplasmosis" include prophylactic use to prevent toxoplasmosis as well as use to treat toxoplasmosis after infection has occurred. The terms "control of malaria" and "controlling malaria" include prophylactic use to prevent malaria as well as use to treat malaria after infection has occurred. The terms "control of African trypanosomiasis" and "controlling African trypanosomiasis" include prophylactic use to prevent African trypanosomiasis as well as use to treat African trypanosomiasis after infection has occurred. The terms "control of Chagas disease" and "controlling Chagas disease" include prophylactic use to prevent Chagas disease as well as use to treat Chagas disease after infection has occurred. The terms "control of opportunistic infection" and "controlling opportunistic infection" include prophylactic use to prevent opportunistic infection(s) as well as use to treat opportunistic infection(s) after infection has occurred.

The invention includes methods of controlling toxoplasmosis, malaria, African trypanosomiasis, Chagas disease and opportunistic infections in a mammal comprising administering a compound of Formula (I) or (II) in an amount which is effective for controlling said disease or condition.

The dosage for the instant compounds can vary according to many factors, including the type of disease, the age and general condition of the patient, the particular compound administered, and the presence or level of toxicity or adverse effects experienced with the drug. A representative example of a suitable dosage range is from as low as about 0.025 mg to about 1000 mg. However, the dosage administered is generally left to the discretion of the physician.

The methods of treatment and prevention can be carried out by delivering the compound of Formula I parenterally. The term 'parenteral' as used herein includes intravenous, intramuscular, or intraperitoneal administration. The instant invention can also be carried out by delivering the compound of Formula (I) or (II) through subcutaneous, intranasal, intrarectal, transdermal or intravaginal routes.

The compounds of Formula (I) or (II) may also be administered by inhalation. By 'inhalation' is meant intranasal and oral inhalation administration. Appropriate dosage forms for such administration, such as an aerosol formulation or a metered dose inhaler, may be prepared by conventional techniques.

The invention also relates to a pharmaceutical composition for mammalian patients comprising a compound of Formula (I) or (II) and a pharmaceutically acceptable carrier. The compounds of Formula (I) or (II) may also be included in pharmaceutical compositions in combination with one or more other therapeutically active, or prophylactically active, compounds. For example, a composition according to the instant invention can include a combination of antiprotozoal compounds comprising a compound of Formula (I) or (II) and other antiprotozoal agent(s).

The pharmaceutical carrier employed can be, for example, a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms for mammalian patients can be employed. If a solid dosage is used for oral administration, the preparation can be in the form of a tablet, hard gelatin capsule, troche or lozenge. The amount of solid carrier will vary widely, but generally the amount of the present compound will be from about 0.025 mg to about 1 g, with the amount of solid carrier making up the difference to the desired tablet, hard gelatin capsule, troche or lozenge size. Thus, the tablet, hard gelatin capsule, troche or lozenge conveniently would have, for example, 0.025 mg, 0.05 mg, 0.1 mg, 0.5 mg, 1 mg, 5 mg, 10 mg, 25 mg, 100 mg, 250 mg, 500 mg, or 1000 mg of the present compound. The tablet, hard gelatin capsule, troche or lozenge is given conveniently once, twice or three times daily.

When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of Formula (I) or (II) used topically will, of course, vary with the compound chosen, the nature and severity of the condition, and can be varied in accordance with the discretion of the physician. A representative topical dose of a compound of Formula (I) or (II) is from as low as about 0.01 mg to as high as about 2.0 g, administered one to four times, preferably one to two times daily.

When used topically, the instant compound may comprise from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container, which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenyl-mercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol, or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Compounds of the present invention can be evaluated by the following in vivo anticoccidiosis assay.

In vivo Anticoccidiosis Assay:

One-day-old White Leghorn chickens are obtained from a commercial hatchery and acclimated in a holding room. At three days of age the test animals are selected by weight, wingbanded, and randomly placed on medicated or control diets for the duration of the experiment. One or two replicates of two birds are utilized per treatment. Following 24 hours premedication, in each replicate one bird is infected with *Eimeria acervulina*, the other bird is infected with *E. tenella*. Both strains of *Eimeria* are sensitive to all anticoccidial products, and have been maintained in laboratory conditions for over 25 years. The inocula consist of sporulated oocysts in tap water suspensions, administered at a dose rate of 0.25 ml per bird. The inocula levels are selected by previous dose titrations to provide a low to moderate level of infection. The *E. acervulina* portion of the experiment is terminated on Day 5, the *E. tenella* on Day 6 post infection. The measured parameters are weight gain, feed consumption and oocyst production. *E. tenella* lesion scores are also recorded for background information. Treatments which provide at least 80% reduction in oocyst production are considered active, those with 50-79% are considered partially active, and those with <50% are considered poorly active. The same numerical categories in weight gain and feed consumption differentiate among treatments with good, fair or poor productivity.

METHODS OF SYNTHESIS

Compounds of the present invention can be prepared according to the Schemes provided below as well as the procedures provided in the Examples. The substituents are the same as in the above Formulas except where defined otherwise or otherwise apparent to the ordinary skilled artisan.

It is understood that the functional groups present in compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

SCHEME I

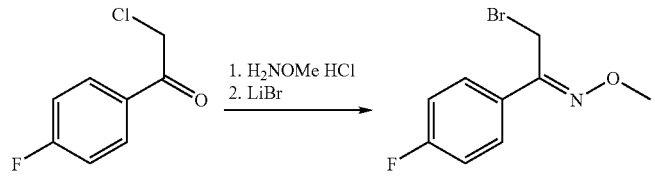

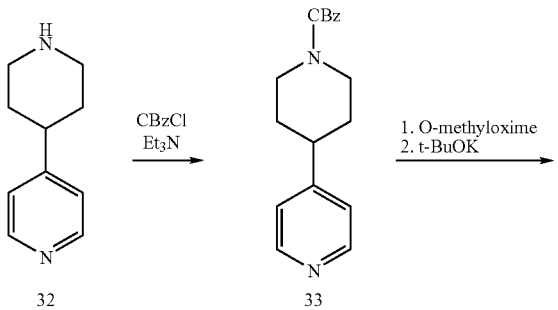

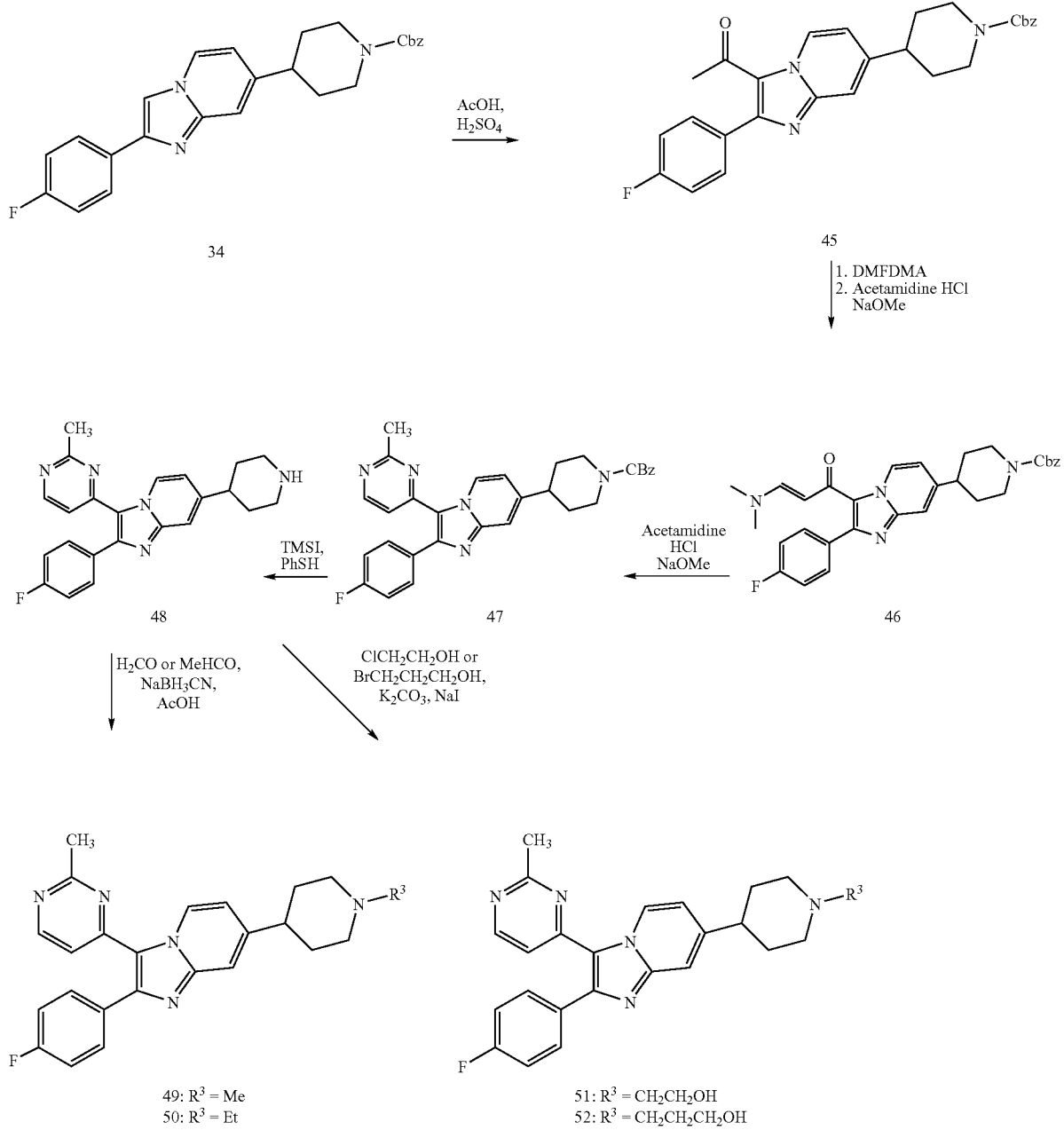

4-fluorophenacyl chloride reacts with O-methylhydroxylamine hydrochloride and forms O-methyloxime 30 when heated for about two hours in solvents such as methanol to about 60° C. Stirring a solution of N-protected pyridyl piperidine 33 with the O-methyloxime 30 in solvents such as acetone until pyridinyl salt formation is almost complete followed by evaporation, dissolving obtained residue in methanol and heating the resulting solution in the presence of a base such as potassium tert-butoxide forms imidazopyridine 34. Heating a solution of 34 in acetic anhydride in the presence of several drops of sulfuric acid for about 48 hours gives the ketone 45. Treatment of ketone 45 dissolved in DW-DMA and heating to about 100° C. for about 12 hours gives the enone 46. When the enone 46 was dissolved in 1-propanol and reacted with a selected amidine hydrochloride in the presence of a base such as sodium methoxide in methanol and heated to about 100° C. for 12 hours, the piperidine 47 is formed in good yield. The CBz protected group can be removed by using reagents such as iodotrimethylsilane or hydrogen gas in the presence of a catalyst such as Pd on carbon to give piperidine 48. The piperidine nitrogen from compound 48 obtained as such can be allylated by treating the amine with alkyl halide in the presence of a base or by reductive amination with an aldehyde or ketone in the presence of a reducing agent such as sodium triacetoxy borohydride to give compounds 49-52.

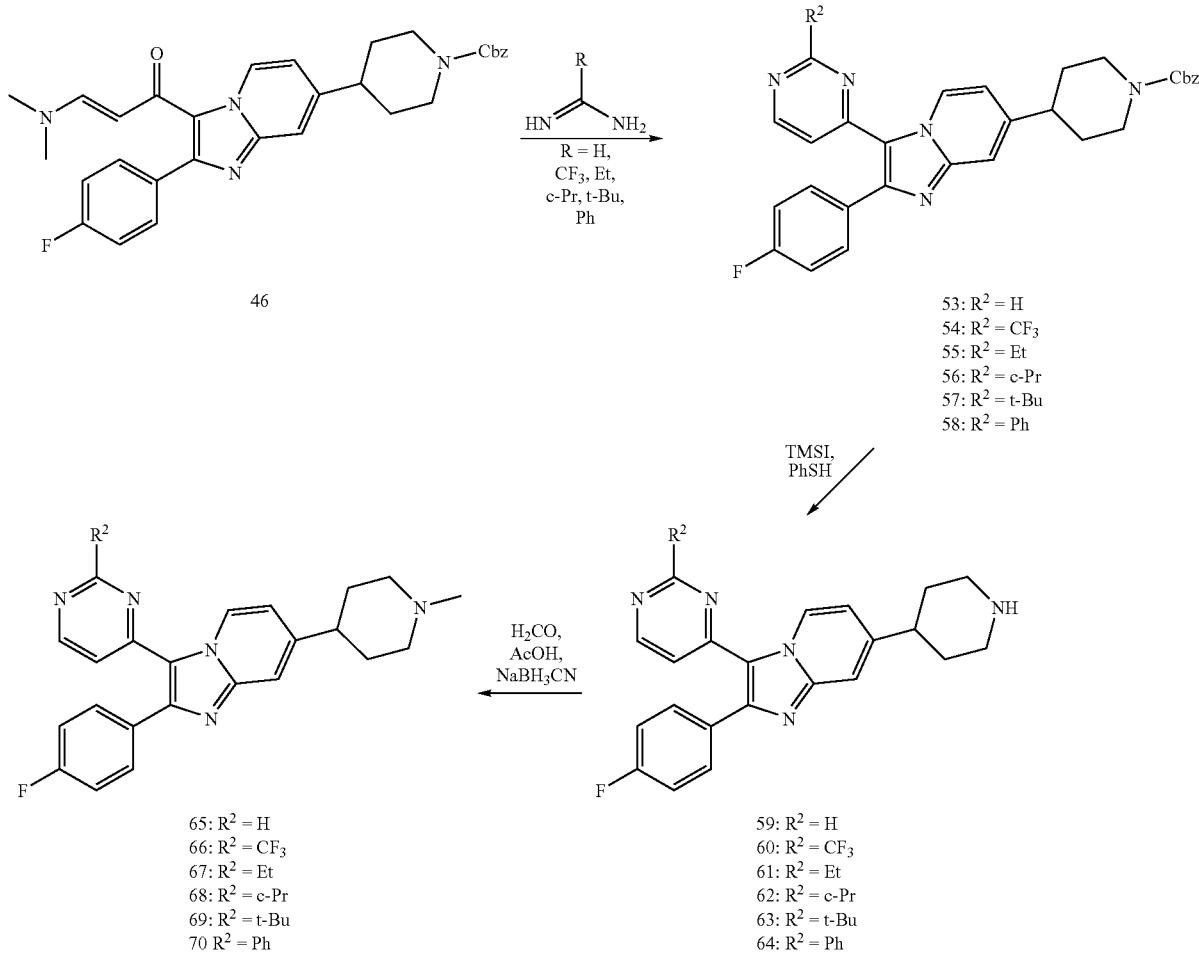
Compounds 59-70 above can synthesized using the procedures described in Scheme 1.
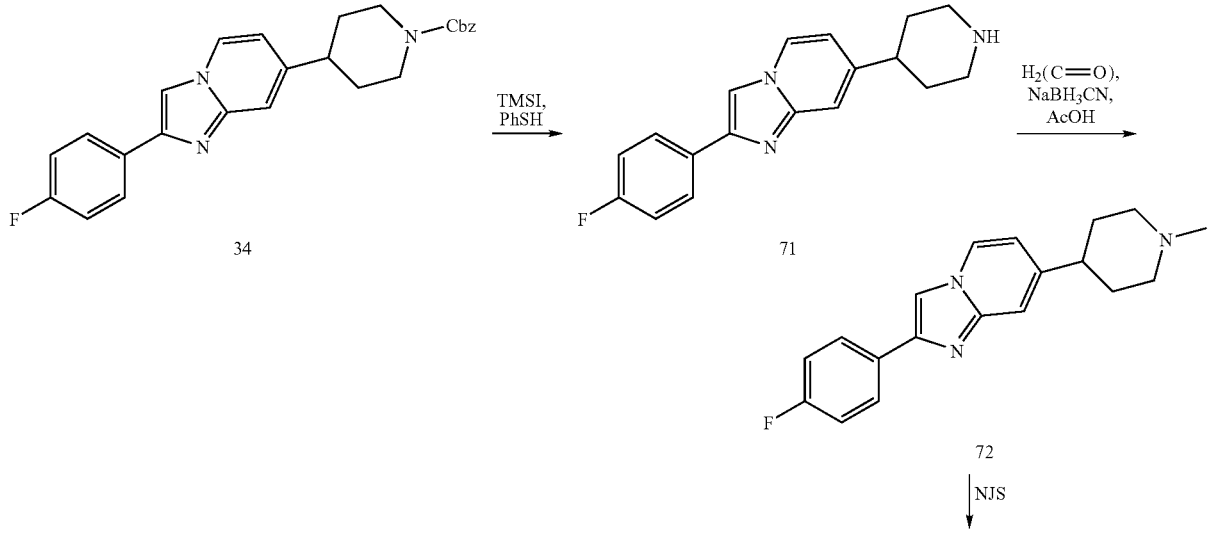

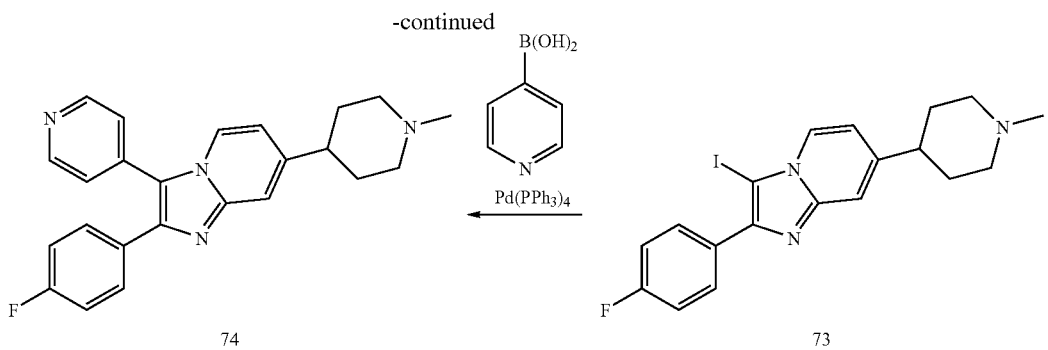

Benzyl carbamate 34 can be deprotected with reagents such as iodotrimethylsilane or with hydrogen in the presence of catalyst such as Pd on carbon to give compound 71. The piperidine nitrogen can be alkylated as shown above in Scheme 1. Halogenation of the 3-postion of imidazopyridine 72 could be carried out with N-iodosuccinimide or N-bromosuccinimide in solvents such as methylene chloride gives compound 73. Heating compound 73 to about 85° C. in the presence of water with boronic acids such as pyridine-4-boronic acid and Pd(PPh$_3$)$_4$ and NaOH for about 12 hours gives the desired product 74.

EXAMPLE 1

2-(4-Fluorophenyl)-7-(1-methylpiperidin-4-yl)-3-(2-methylpyrimidin-4-yl)imidazo[1,2-a]-pyridine

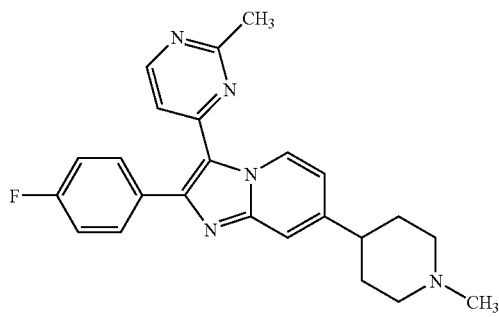

Step 1. A 2.0 L round bottom flask was charged with 4-fluorophenacyl chloride (100 g, 579 mmol), then methanol (1.0 L), then O-methylhydroxylamine HCl (96.8 g, 1.56 mol), and the mixture was heated to 65° C. for 2 hours. The reaction was then concentrated under reduced pressure, then charged with acetone (750 mL), and lithium bromide (252 g, 2.90 mol), and the mixture was heated to 60° C. for 16 hours. The reaction was then concentrated under reduced pressure, suspended in 1.0 L methylene chloride, and washed with 3×200 mL water. All organic extracts were then pooled; dried over Na$_2$SO$_4$, filtered, and concentrated under reduced pressure to yield 2-bromo-1-(4-fluorophenyl)ethanone O-methyloxime (118 g, 83%). $^1$H NMR (500 MHz, CDCl$_3$) δ 4.10 (s, 3H), 4.35 (s, 2H), 7.11 (t, J=8.8 Hz, 2H), 7.72 (m, 2H). MS (ESI+) 246.0.

Step 2. A 2.0 L round bottom flask was charged with 4-(piperidin-4-yl)pyridine (69.0 g, 425 mmol), methylene chloride (500 mL), and then triethylamine (47.0 g, 468 mmol). CbzCl (80.0 g, 468 mmol) was then added dropwise over 30 minutes via an addition funnel. The reaction was allowed to stir at room temperature for 18 hours. The reaction was then poured into 500 mL of an aqueous solution saturated with NaHCO$_3$ and extracted with an additional 300 mL of methylene chloride. The organic fractions were pooled, dried over Na$_2$SO$_4$, filtered, and concentrated under reduced pressure. The crude product (135 g, 104% yield) was dissolved in 200 mL methylene chloride and applied onto a silica plug that was then eluted with 2.0 L heptane, 3.0 L 1:1 EtOAc:heptane, 1.5 L 2:1 EtOAc:heptane, and 3.0 L EtOAc, collecting 750 mL fractions. Fractions containing desired product were pooled and concentrated under reduced pressure to provide benzyl 4-(pyridin-4-yl)piperidine-1-carboxylate (93.5 g, 74%). $^1$H NMR (500 MHz, CDCl$_3$) δ 1.87 (m, 2H), 2.30 (m, 2H), 2.69 (m, 1H), 2.91 (bs, 2H), 4.37 (bs, 2H), 5.17 (m, 2H), 7.13 (d, J=6.3 Hz, 2H), 7.39 (m, 5H), 8.54 (d, J=6.3 Hz, 2H). MS (ESI+) 297.1.

Step 3. A 2.0 L round bottom flask was charged with pyridine, the compound of Step 2 (88.6 g, 299 mmol), acetone (300 mL), and the compound of Step 1 (73.8 g, 30.0 mmol), followed by additional acetone (200 mL). The reaction was allowed to stir at room temperature for 12 hours, after which TLC analysis was performed to determine formation of pyridinyl salt. The reaction was then concentrated under reduced pressure, charged with methanol (500 mL), and then potassium tert-butoxide (44.3 g, 395 mmol) in small portions. The mixture was then heated to 80° C. for 4 hours. The reaction was then allowed to stir at room temperature for 12 hours, and was then concentrated under reduced pressure, and then slurried in 200 mL methylene chloride with <5% methanol, then loaded onto a silica plug that was eluted with 2.0 L heptane, 3.0 L 1:2-EtOAc:heptane, 1.5 L 1:1 EtOAc:heptane, and 2.0 L EtOAc, collecting 750 mL fractions. Fractions containing pure desired product were pooled and concentrated under reduced pressure to yield benzyl 4-[2-(4-fluorophenyl)imidazo[1,2-a]pyridin-7-yl]piperidine-1-carboxylate (74.6 g, 58%); fractions containing impure desired product were pooled and concentrated under reduced pressure to yield additional desired compound (21 g, 16%). $^1$H NMR (500 MHz, CDCl$_3$) δ 1.50 (m, 2H), 1.76 (m, 2H), 2.55 (m, 1H), 2.77 (bs, 2H), 4.45 (bs, 2H), 5.04 (s, 2H), 6.48 (d, J=5.3 Hz, 1H), 6.96 (t, J=8.8 Hz, 2H), 7.24 (m, 6H), 7.57 (s, 1H), 7.76 (m, 2H), 7.86 (d, J=7.1 Hz, 1H). MS (ESI+) 430.2.

Step 4. Benzyl 4-[2-(4-fluorophenyl)imidazo[1,2-a]pyridin-7-yl]piperidine-1-carboxylate (Step 3, 74.6 g, 174 mmol) was dissolved in acetic anhydride (1.0 L) in a 2.0 L round bottom flask. Seven drops of sulfuric acid were then added, and the reaction was heated to 125° C. for 20 hours, then 150° C. for 40 hours, and then 170° C. for 24 hours. The reaction was concentrated under reduced pressure, then diluted with 150 mL methylene chloride, and applied onto a silica plug that was eluted with 3.0 L heptane, 6.0 L 1:2 EtOAc:heptane, 3.0 L 1:1 EtOAc:heptane, and 4.0 L EtOAc 750 mL fractions were collected throughout the chromatography process. Fractions containing desired product still contaminated with starting material were pooled and concentrated under reduced pressure to provide benzyl 4-[3-acetyl-2-(4-fluorophenyl)imidazo-[1,2-a]pyridin-7-yl]piperidine-1-carboxylate (45.9 g, 82% pure by HPLC). Additional desired compound crystallized from several of the chromatography fractions, and was filtered and dried (10.8 g, 100% pure by HPLC). Both pure and impure batches were pooled and carried onto the next step. Overall yield of desired compound: 56.7 g total, or 48.4 g pure (59%). $^1$H NMR (400 MHz, CDCl$_3$) δ 1.67 (m, 2H), 1.92 (m, 2H), 2.17 (s, 3H), 2.81 (m, 1H), 2.93 (bs, 2H), 4.38 (bs, 2H), 5.16 (s, 2H), 6.48 (d, J=7.2 Hz, 1H), 6.96 (t, J=8.8 Hz, 2H), 7.24 (m, 5H), 7.57 (s, 1H), 7.76 (m, 2H), 7.86 (d, J=7.2 Hz, 1H). MS (ESI+) 472.2.

Step 5. Benzyl 4-[3-acetyl-2-(4-fluorophenyl)imidazo[1,2-a]pyridin-7-yl]piperidine-1-carboxylate (Step 4, 3.12 g, 6.62 mmol) was dissolved in DMF-DMA (50 mL) and heated to 100° C. for 12 hours. The reaction was concentrated under reduced pressure, then dissolved in a minimum volume of methylene chloride, and injected onto an Isco RediSep 40 g normal phase cartridge, and eluted with a gradient that started with 100% heptane and ended with 100% ethyl acetate. The cartridge was then eluted with 90:9:1 methylene chloride:methanol:concentrated ammonium hydroxide. Fractions containing desired product were pooled and concentrated under reduced pressure to provide benzyl 4-{3-[(2E)-3-(dimethylamino)prop-2-enoyl]-2-(4-fluorophenyl)imidazo[1,2-a]pyridin-7-yl}piperidin-1-carboxylate (2.50 g, 72%). MS (ESI+) 527.3.

Step 6. Benzyl 4-{3-[(2E)-3-(dimethylamino)prop-2-enoyl]-2-(4-fluorophenyl)imidazo-[1,2-a]pyridin-7-yl}piperidin-1-carboxylate (Step 5, 1.32 g, 2.52 mmol) was dissolved in 1-propanol (20 mL) and charged with acetamidine HCl (945 mg, 10.0 mmol) and 25% (w/w) sodium methoxide in methanol (2.29 mL, 10.0 mmol), and heated to 100° C. for 12 hours. The reaction mixture was then concentrated under reduced pressure, suspended in methylene chloride (20 mL), and washed with 3×50 mL saturated aqueous NaHCO$_3$ solution. The organic phase was then dried over Na$_2$SO$_4$, filtered, concentrated under reduced pressure, then dissolved in a minimum volume of methylene chloride and injected onto an Isco RediSep 40 g normal phase cartridge, and eluted with a gradient that started with 100% heptane and ended with 100% ethyl acetate. Fractions containing desired product were pooled and concentrated under reduced pressure to provide benzyl 4-[2-(4-fluorophenyl)-3-(2-methylpyrimidin-4-yl)imidazo[1,2-a]pyridin-7-yl]piperidine-1-carboxylate (1.17 g, 89%). MS (ESI+) 522.4.

Step 7. Benzyl 4-[2-(4-fluorophenyl)-3-(2-ethylpyrimidin-4-yl)imidazo[1,2-a]pylidin-7-yl]piperidine-1-carboxylate (Step 6, 1.17 g, 2.24 mmol) was dissolved in acetonitrile (100 mL) and charged with thiophenol (3.36 mmol, 346 µL), then iodotrimethylsilane (22.4 mmol, 3.18 mL). After stirring at room temperature for 30 minutes, the reaction was concentrated under reduced pressure, then dissolved in a minimum volume of methylene chloride and injected onto an Isco RediSep 40 g normal phase cartridge, and eluted with a gradient that started with 100% methylene chloride and ended with 100% 90:9:1 methylene chloride:methanol:concentrated ammonium hydroxide. Fractions containing desired product were pooled, then concentrated under reduced pressure to provide crude 2-(4-fluorophenyl)-3-(2-methylpyrimidin-4-yl)-7-piperidin-4-ylimidazo[1,2-a]pyridine (1.44 g,>100%), which was carried on to the next step without further purification. $^1$H NMR (400 MHz, CDCl$_3$) δ 2.04 (m, 6H), 2.82 (s, 3H), 2.90 (m, 1H), 3.42 (m, 2H), 4.75 (bs, 1H), 6.90 (d, 3=7.4 Hz, 1H), 6.95 (d, J=5.6 Hz, 1H), 7.13 (m, 2H), 7.54 (s, 1H), 7.59 (m, 2H), 8.39 (d, J=5.5 Hz, 1H), 9.61 (d, J=7.4 Hz, 1H). MS (ESI+) 388.3.

Step 8. 2-(4-fluorophenyl)-3-(2-methylpyrimidin-4-yl)-7-piperidin-4-ylimidazo[1,2-a]-pyridine (Step 7, 750 mg, 1.93 mmol) was dissolved in methanol (50 mL), and charged with acetic acid (750 µL), formaldeyhyde (37% w/w in water, 7.74 mmol, 576 µL), and NaBH$_3$CN (9.68 mmol of a 1.0M solution in THF, 9.68 mL). After stirring for 45 minutes at room temperature, the reaction was concentrated under reduced pressure, dissolved in methanol (12 mL), and purified via 24×0.5 mL injections on a reverse phase HPLC column using a gradient that started with 50% methanol: 50% 0.1% Et$_3$N in water and ended with 100% methanol. Fractions containing desired product were pooled and concentrated under reduced pressure to provide the title compound. $^1$H NMR (400 MHz, CDCl$_3$) δ 1.92 (m, 4H), 2.12 (m, 2H), 2.35 (s, 3H), 2.59 (m, 1H), 2.81 (s, 3H), 3.05 (m, 2H), 6.88 (dd, J=7.3, 1.8 Hz, 1H), 6.94 (d, J=5.5 Hz, 1H), 7.12 (m, 2H), 7.51 (s, 1H), 7.60 (m, 2H), 8.38 (d, J=5.6 Hz, 1H), 9.59 (dd, J=7.3, 0.77 Hz, 1H). MS (ESI+) 402.3.

EXAMPLE 2

7-(1-Ethylpiperidin-4-yl)-2-(4-fluorophenyl)-7-3-(2-methylpyrimidin-4-yl)imidazo[1,2-a]-pyridine

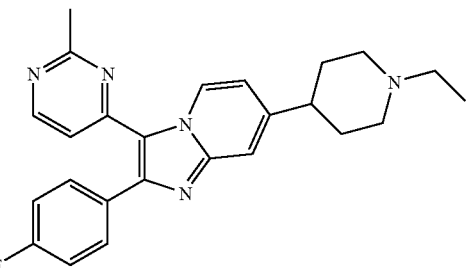

2-(4-fluorophenyl)-3-(2-methylpyrimidin-4-yl)-7-piperidin-4-ylimidazo[1,2-a]-pyridine (Example 1, Step 7, 300 mg, 0.774 mmol) was dissolved in methanol (5 mL), and charged with acetic acid (300 µL), acetaldeyhyde (0.85 mmol, 48 µL), and NaBH$_3$CN (0.929 mmol of a 1.0M solution in THF, 929 µL). After stirring for 15 minutes at room temperature, the reaction was quenched with 1 mL concentrated ammonium hydroxide, then purified via 6×1.0 mL injections onto a reverse phase HPLC column using a gradient that started with 40% methanol: 60% 0.1% Et$_3$N in water and ended with 100% methanol. Fractions containing desired product were pooled and concentrated under reduced pressure to provide the title compound (119 mg, 37%). $^1$HNMR (400 MHz, CDCl$_3$) δ 1.15 (t, J=7.2 Hz, 3H), 1.94 (m, 4H), 2.10 (m, 2H), 2.50 (m, 2H), 2.63 (m, 1H), 2.81 (s, 3H), 3.13 (m, 2H), 6.90 (dd, J=7.4, 1.9 Hz, 1H), 6.94 (d, J=5.4 Hz, 1H), 7.12 (m, 2H), 7.58 (s, 1H), 7.59 (m, 2H), 8.38 (d, J=5.5 Hz, 1H), 9.59 (dd, J=7.2, 0.6 Hz, 1H). MS (ESI+) 416.2.

EXAMPLE 3

2-{4-[2-Fluorophenyl-3-(2-methylprirmidin-4-yl)imidazo[1,2-a]pyridin-7-yl]piperidin-1-yl}-ethanol

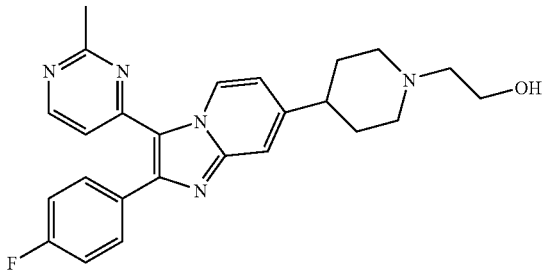

2-(4-fluorophenyl)-3-(2-methylpyrimidin-4-yl)-7-piperidin-4-ylimidazo[1,2-a]-pyridine (Example 1, Step 7, 150 mg, 0.387 mmol) was dissolved in ethanol (10 mL), and charged with 2-chloroethanol (0.46 mmol, 37 mg, 31 μL), sodium iodide (0.04 mmol, 6 mg), and potassium carbonate (0.968 mmol, 134 mg), and the mixture was heated to 90° C. for 36 hours. The reaction was diluted with 200 mL methylene chloride, then washed with 100 mL saturated aqueous NaHCO$_3$ solution. The aqueous phase was then back extracted with 2×100 mL methylene chloride. The organic fractions were then pooled, dried over Na$_2$SO$_4$, filtered, and concentrated under reduced pressure. The fractions were then dissolved in a minimum volume of methylene chloride, injected onto an Isco RediSep 40 g normal phase cartridge, and eluted with a gradient that started with 100% methylene chloride and ended with 100% 90:9:1 methylene chloride:methanol:concentrated ammonium hydroxide. Fractions containing desired product were pooled, then concentrated under reduced pressure. This concentrate was then dissolved in 11.0 mL of methanol, and purified via 11×1.0 mL injections onto a reverse phase DPLC column using a gradient that started with 40% methanol: 60% 0.1% Et$_3$N in water and ended with 100% methanol. Fractions containing desired product were pooled and concentrated under reduced pressure to provide title compound (67 mg, 42%). $^1$H NMR (400 MHz, CDCl$_3$) δ 1.83 (m, 2H), 1.93 (m, 2H), 2.25 (dd, J=11.6, 10.2 Hz, 2H), 2.60 (t, J=5.3 Hz, 2H), 2.64 (m, 1H), 2.81 (s, 3H), 3.09 (m, 2H), 3.65 (d, J=5.4 Hz, 2H), 6.89 (dd, J=7.3, 1.5 Hz, 1H), 6.95 (d, J=5.4 Hz, 1H), 7.12 (m, 2H), 7.50 (s, 1H), 7.60 (m, 2H), 8.38 (d, J=5.6 Hz, 1H), 9.60 (d, J=7.3 Hz, 1H). MS (ESI+) 432.3.

EXAMPLE 4

3-{4-[2-Fluorophenyl-3-(2-methylpyrimidin-4-yl)imidazo[1,2-a]pyridin-7-yl]piperidin-1-yl}-propanol

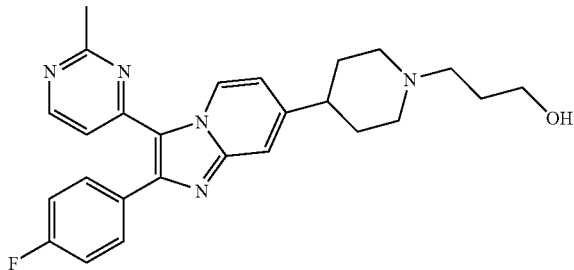

2-(4-fluorophenyl)-3-(2-methylpyrimidin-4-yl)-7-piperidin-4-ylimidazo[1,2-a]-pyridine (Example 1, Step 7, 150 mg, 0.387 mmol) was dissolved in ethanol (10 mL), and charged with 3-bromopropanol (0.46 mmol, 64 mg, 40 μL), and potassium carbonate (0.968 mmol, 134 mg). The mixture was heated to 90° C. for 12 hours, after which additional 3-bromopropanol (0.46 mmol, 64 mg, 40 μL) was added. After stirring for 4 additional hours at 90° C., the reaction was diluted with 100 mL methylene chloride, then washed with 50 mL saturated aqueous NaHCO$_3$ solution. The aqueous phase was then back extracted with 2×50 mL methylene chloride. The organic fractions were then pooled, dried over Na$_2$SO$_4$, filtered, concentrated under reduced pressure, then dissolved in 8.0 mL of methanol, and purified via 16×0.5 mL injections onto a reverse phase TPLC column using a gradient that started with 50% methanol: 50% 0.1% Et$_3$N in water and ended with 100% methanol. Fractions containing desired product were pooled and concentrated under reduced pressure to provide title compound (110 mg, 63%). $^1$H NMR (400 MHz, CDCl$_3$) δ 1.77 (m, 4H), 1.94 (m, 2H), 2.12 (m, 2H), 2.66 (m, 1H), 2.67 (t, J=5.6 Hz, 2H), 2.81 (s, 3H), 3.24 (m, 2H), 3.83 (t, J=5.1 Hz, 2H), 6.87 (dd, J=7.3, 1.2 Hz, 1H), 6.94 (d, J=5.5 Hz, 1M), 7.12 (m, 2H), 7.48 (s, 1H), 7.59 (m, 2H), 8.38 (d, J=5.5 Hz, 1H), 9.59 (d, J=7.3 Hz, 1H). MS (ESI+) 446.2.

EXAMPLE 5

2-(4-Fluorophenyl)-7-(1-methylpiperidin-4-yl)-3-(pyrimidin-4-yl)imidazo[1,2-a]pyridine

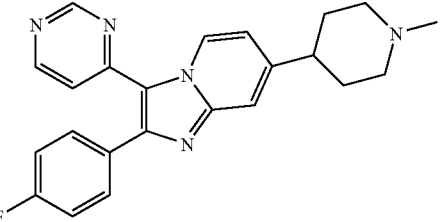

Step 1. Benzyl 4-{3-[(2E)-3-(dimethylamino)prop-2-enoyl]-2-(4-fluorophenyl)imidazo-[1,2-a]pyridin-7-yl}piperidin-1-carboxylate (Example 1, Step 5, 0.570 mmol, 300 mg) was charged with 1-propanol (5 mL), formamidine HCl (2.28 mmol, 183 mg), and sodium methoxide (2.28 mmol, 0.521 mL of a 25% w/w solution in methanol). This reaction was heated to 100° C. for 12 hours. The reaction was then poured into a separatory funnel, diluted with methylene chloride (100 mL), washed with 50 mL saturated aqueous NaHCO$_3$ solution, dried over Na$_2$SO$_4$, filtered, concentrated under reduced pressure, then dissolved in a minimum volume of methylene chloride and injected onto an Isco RediSep 40 g normal phase cartridge, and eluted with a gradient that started with 100% heptane and ended with 100% ethyl acetate. Fractions containing desired product were pooled and concentrated under reduced pressure to provide benzyl 4-[2-(4-fluorophenyl)-3-(pyrimidin-4-yl)imidazo[1,2-a]pyridin-7-yl]piperidine-1-carboxylate (191 mg, 66%). MS (ESI+) 508.4.

Step 2. Benzyl 4-[2-(4-fluorophenyl)-3-(pyrimidin-4-yl)imidazo[1,2-a]pyridin-7-yl]-piperidine-1-carboxylate (Step 1, 0.368 mmol, 187 mg) was diluted with acetonitrile, then charged with thiophenol (0.553 mmol, 61 mg, 57 μL), and iodotrimethylsilane (3.68 mmol, 737 mg, 524 μL), and the reaction stirred at room temperature for 12 hours. The reaction was concentrated under reduced pressure, then dissolved in a minimum volume of methylene chloride and injected onto an Isco RediSep 40 g normal phase cartridge, and eluted with a gradient that started with 100% methylene chloride and ended with 100% 90:9:1 methylene chloride:methanol:concentrated ammonium hydroxide. Fractions containing desired product were pooled and concentrated under reduced pressure to provide 2-(4-fluorophenyl)-3-(pyrimidin-4-yl)-7-piperidin-4-ylimidazo[1,2-a]pyridine (130 mg, 94%). MS (ESI+) 374.3.

Step 3. 2-(4-fluorophenyl)-3-(pyrimidin-4-yl)-7-piperidin-4-ylimidazo[1,2-a]pyridine (Step 2, 0.348 mmol, 130 mg) was diluted in methanol (5.0 mL), then charged with acetic acid (130 μL), 37% w/w formaldehyde in water (0.383 mmol, 31 mg, 29 μL), and NaBH$_3$CN (0.418 mmol, 418 μL of a 1.0M solution in THF). After stirring at room temperature for 30 minutes, the reaction was quenched with 1.0 mL concentrated ammonium hydroxide, then purified via 6×1.0 mL injections onto a reverse phase HPLC column using a gradient that started with 50% methanol:50% 0.1% Et$_3$N in water and ended with 100% methanol. Fractions containing desired product were pooled and concentrated under reduced pressure to provide the title compound (96 mg, 71%). $^1$H NMR (400 MH, CDCl$_3$) δ 1.91 (m, 4H), 2.10 (m, 2H), 2.35 (s, 3H), 2.59 (m, 1H), 3.02 (m, 2H), 6.89 (dd, J=7.3, 1.9 Hz, 1H), 7.14 (m, 3H), 7.58 (s, 1H), 7.60 (m, 2H), 8.45 (d, 3=5.5 Hz, 1H), 9.25 (s, 1H), 9.65 (dd, J=7.3, 0.7 Hz, 1H). MS (ESI+) 388.3.

EXAMPLE 6

2-(4-Fluorophenyl)-7-(1-methylpiperidinyl)-3-(2-trifluoromethylprimdin-4-yl)imidazo-[1,2-a]pyridine

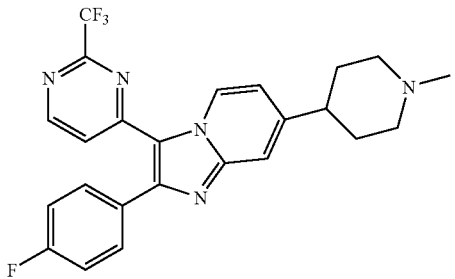

Benzyl 4-{3-[(2E)-3-(dimethylamino)prop-2-enoyl]-2-(4-fluorophenyl)imidazo-[1,2-a]pyridin-7-yl}piperidin-1-carboxylate (Example 1, Step 5, 0.570 mmol, 300 mg) was charged with 1-propanol (5 mL), trifluoroacetamidine (2.28 mmol, 255 mg), and sodium methoxide (2.28 mmol., 0.521 mL of a 25% w/w solution in methanol). This reaction was heated to 100° C. for 12 hours. At this point, additional trifluoroacetamidine (4.56 mmol, 510 mg) was added, and heating continued for 6.5 hours. The reaction was then poured into a separatory funnel, diluted with methylene chloride (100 mL), washed with 50 mL saturated aqueous NaHCO$_3$ solution, dried over Na$_2$SO$_4$, filtered, concentrated under reduced pressure, then dissolved in a minimum volume of methylene chloride and injected onto an Isco RediSep 40 g normal phase cartridge, and eluted with a gradient that started with 100% heptane and ended with 100% ethyl acetate. Fractions containing desired product were pooled and concentrated under reduced pressure to provide benzyl 4-[2-(4-fluorophenyl)-3-(2-trifluoromethylpyrimidin-4-yl)imidazo[1,2-a]pyzidin-7-yl]piperidine-1-carboxylate.

Using the above compound and following the procedures of Example 5, Steps 2 and 3, the title compound was obtained. $^1$H NMR (400 MHz, CDCl$_3$) δ 1.92 (m, 4H), 2.12 (m, 2H), 2.36 (s, 3H), 2.62 (m, 1H), 3.02 (m, 2H), 6.99 (dd, 3=7.4, 1.9 Hz, 1H), 7.18 (m, 3H), 7.24 (m, 1H), 7.56 (s, 1H), 7.60 (m, 1H), 8.53 (d, J=5.6 Hz, 1H), 9.73 (dd, J=7.3, 0.7 Hz, 1H). MS (ESI+) 456.3.

EXAMPLE 7

3-(2-Ethylpyrimidin-4-yl)-2-(4-fluorophenyl)-7-(1-methylpiperidin-4-yl)imidazo[1,2-a]pyridine

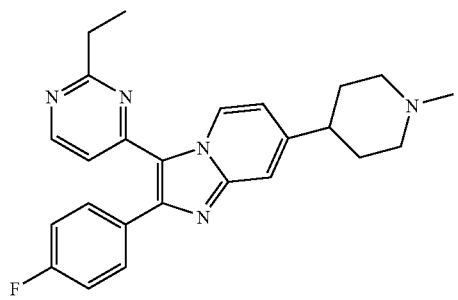

The procedures described in Example 5 were followed, except that in Step 1, propionamidine HCl was used instead of formamidine HCl. After heating this initial reaction mixture to 100° C. for 12 hours, additional propionamidine HCl (2× initial amount) and sodium methoxide (2× initial amount) were added, and heating continued for 6.5 hours, to provide the title compound. $^1$H NMR (400 MHz, CDCl$_3$) δ 1.47 (t, J=7.6 Hz, 3H), 1.93 (m, 4H), 2.13 (m, 2H), 2.37 (m, 3H), 2.60 (m, 1H), 3.05 (m, 2H), 3.08 (q, J=7.6 Hz, 2H), 6.89 (d, J=7.3, 1.8 Hz, 1H), 6.95 (d, J=5.5 Hz, 1H), 7.12 (m, 2H), 7.51 (s, 1H), 7.60 (m, 2H), 8.40 (d, J=5.4 Hz, 1H), 9.65 (dd, J=7.3, 0.5 Hz, 1H). MS (ESI+) 416.3.

EXAMPLE 8

3-(2-Cyploroylpyrimdin-4-yl)-2-(4-fluoropheneyl)-7-(1-methylpiperidin-4-yl)imidazo-[1,2-a]pyridine

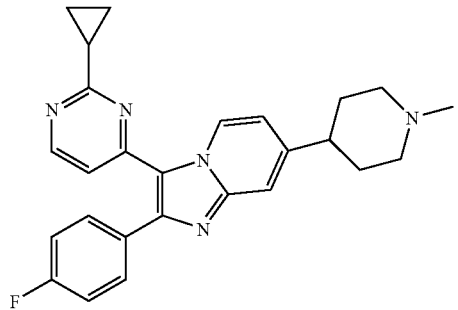

The procedures described in Example 5 were followed to provide the title compound, except that in Step 1, cyclopropylcarbamidine HCl was used instead of formamidine HCl.

¹H NMR (400 Mz, CDCl₃) δ 1.14 (m, 2H), 1.22 (m, 2H), 1.91 (m, 4H), 2.10 (m, 2H), 2.32 (m, 1H), 2.34 (s, 3H), 2.58 (m, 1H), 3.00 (m, 2H), 6.86 (m, 1H), 6.87 (d, J=5.5 Hz, 1H), 7.11 (m, 2H), 7.57 (s, 1H), 7.59 (m, 2H), 8.31 (m, 1H), 9.53 (dd, J=7.2, 0.7 Hz, 1H). MS (ESI+) 428.3.

EXAMPLE 9

3-(2-tert-Butylpyrimidin-4-yl)-2-(4-fluorophenyl)-7-(1-methylpiperidin-4-yl)imidazo[1,2-a]-pyridine

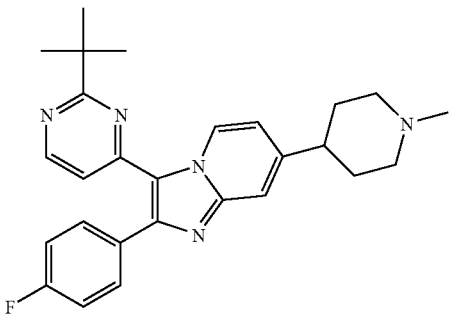

The procedures described in Example 5 were followed to provide the title compound, except that in Step 1, 2,2-dimethylpropionamidine HCl was used instead of formamidine HCl. ¹H NMR (400 MHz, CDCl₃) δ 1.50 (s, 9H), 1.92 (m, 4H), 2.10 (m, 2H), 2.34 (s, 3H), 2.59 (m, 1H), 3.00 (m, 2H), 6.89 (dd, J=7.3, 1.8 Hz, 1H), 6.94 (d, J=5.4 Hz, 1H), 7.13 (m, 2H), 7.52 (s, 1H), 7.61 (m, 2H), 8.44 (d, J=5.4 Hz, 1H), 9.70 (dd, J=7.3, 0.7 Hz, 1H). MS (ESI+) 444.3.

EXAMPLE 10

2-(4-Fluorophenyl)-7-(1-methylpiperidin-4-yl)-3-(2-phenylpyrimidin-4-yl)imidazo[1,2-a]-pyridine

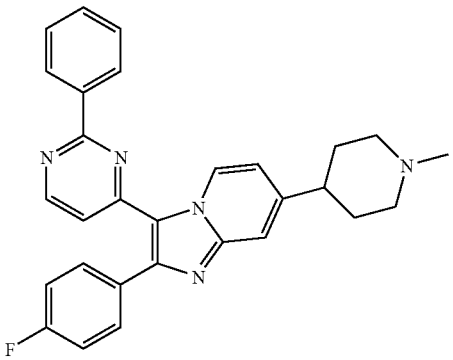

The procedures described in Example 5 were followed to provide the title compound, except that in Step 1, benzamidine HCl was used instead of formamidine HCl. ¹H NMR (400 MHz, CDCl₃) δ 1.93 (m, 4H), 2.10 (m, 2H), 2.34 (s, 3H), 2.60 (m, 1H), 3.05 (m, 2H), 6.92 (dd, J=7.3, 1.8 Hz, 1H), 7.03 (d, J=5.4 Hz, 1H), 7.14 (m, 2H), 7.55 (m, 4H), 7.65 (m, 2H), 8.50 (m, 2H), 8.56 (d, J=5.4 Hz, 1H), 9.63 (d, J=7.3 Hz, 1H). MS (ESI+) 464.3.

What is claimed is:

1. A compound represented by Formula (I)

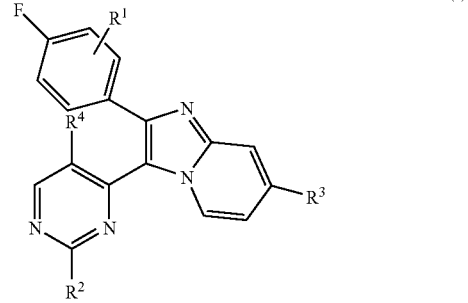

or a pharmaceutically acceptable salt, or N-oxide thereof, wherein

R¹ is
 (a) hydrogen,
 (b) C₁-C₆-alkyl,
 (c) halogen;

R² is
 (a) hydrogen,
 (b) C₁-C₆-alkyl, optionally substituted with one or more of halogen, —OH, or aryl,
 (c) cycloalkyl,
 (d) CF₃,
 (e) aryl, optionally substituted with one or more of halogen or alkyl,
 (f) heteroaryl, optionally substituted with one or more of alkyl or halogen;

R³ is selected from

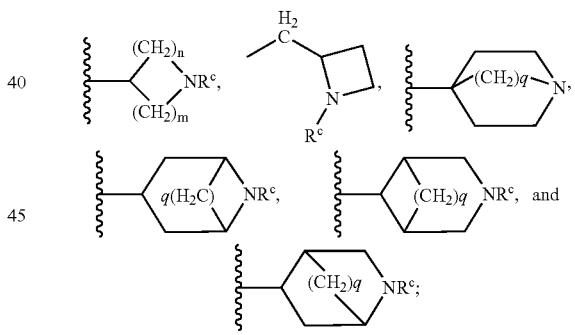

Rᶜ is selected from hydrogen and C₁₋₄alkyl, wherein alkyl is optionally substituted with one or more of halogen or —OH;

n and m are independently 0, 1, 2, 3 or 4, provided that n+m=2, 3 or 4;

q is 1 or 2; and

R⁴ is hydrogen or halogen.

2. The compound of claim 1, or a pharmaceutically acceptable salt, or an N-oxide thereof, wherein
R² is optionally substituted C₁-C₆-alkyl.

3. The compound of claim 1, or a pharmaceutically acceptable salt, or an N-oxide thereof, wherein
R² is cycloalkyl.

4. The compound of claim 1, or a pharmaceutically acceptable salt, or an N-oxide thereof, wherein
R² is CF₃.

5. The compound of claim 1, or a pharmaceutically acceptable salt, or an N-oxide thereof, wherein
R² is optionally substituted aryl.

6. The compound of claim 1, or a pharmaceutically acceptable salt, or an N-oxide thereof, wherein
R² is optionally substituted heteroaryl.

7. The compound of claim 1, or a pharmaceutically acceptable salt, or an N-oxide thereof, wherein

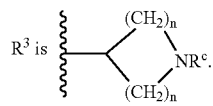

8. The compound of claim 1, or a pharmaceutically acceptable salt, or an N-oxide thereof, wherein

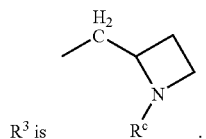

9. The compound of claim 1, or a pharmaceutically acceptable salt, or an N-oxide thereof, wherein

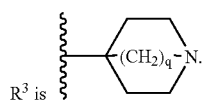

10. The compound of claim 1, or a pharmaceutically acceptable salt, or an N-oxide thereof, wherein

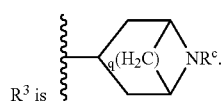

11. The compound of claim 1, or a pharmaceutically acceptable salt, or an N-oxide thereof, wherein

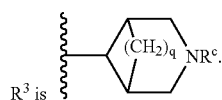

12. The compound of claim 1, or a pharmaceutically acceptable salt, or an N-oxide thereof, wherein

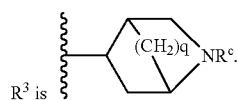

13. The compound of claim 1, or a pharmaceutically acceptable salt, or an N-oxide thereof, wherein
R³ is piperidinyl.

14. The compound of claim 1, or a pharmaceutically acceptable salt, or an N-oxide thereof, wherein
R³ is [($C_{1-4}$) alkyl]piperidinyl.

15. The compound of claim 1, or a pharmaceutically acceptable salt, or an N-oxide thereof, wherein
R³ is piperidin-4-yl.

16. The compound of claim 1, or a pharmaceutically acceptable salt, or an N-oxide thereof, wherein
R³ is [($C_{1-4}$)alkyl]piperidin-4-yl.

17. The compound of claim 1, or a pharmaceutically acceptable salt, or an N-oxide thereof, wherein
R³ is 1-methylpiperidinyl.

18. The compound of claim 1, or a pharmaceutically acceptable salt, or an N-oxide thereof, wherein
R³ is 1-methylpiperidin-4-yl.

19. The compound of claim 1, or a pharmaceutically acceptable salt, or an N-oxide thereof, wherein
R³ is 1-(3-hydroxypropyl)-4-piperidinyl.

20. The compound of claim 1, or a pharmaceutically acceptable salt, or an N-oxide thereof, wherein
R³ is 1-(3-hydroxyethyl)-4-piperidinyl.

21. A compound represented by Formula (II)

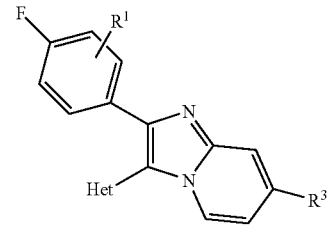

or a pharmaceutically acceptable salt, or N-oxide thereof, wherein
Het is pyridyl, puridazinyl, triazinyl, thiazolyl, or isothiazolyl, optionally substituted with one or more of amino, alkyl or halogen; and
R¹ is
(d) hydrogen,
(e) $C_1$-$C_6$-alkyl,
(f) halogen;

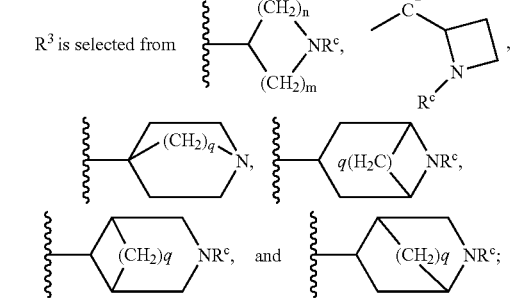

$R^c$ is selected from hydrogen and $C_{1-4}$alkyl, wherein alkyl is optionally substituted with one or more of halogen or —OH;
n and m are independently 0, 1, 2, 3 or 4, provided that n+m =2, 3 or 4; and
q is 1 or 2.

22. The compound of claim 21, or a pharmaceutically acceptable salt, or an N-oxide thereof, wherein Het is pyridyl.

23. The compound of claim 21, or a pharmaceutically acceptable salt, or an N-oxide thereof, wherein Het is pyridazinyl.

24. The compound of claim 21, or a pharmaceutically acceptable salt, or an N-oxide thereof, wherein Het is triazinyl.

25. The compound of claim 21, or a pharmaceutically acceptable salt, or an N-oxide thereof, wherein Het is thiazolyl.

26. The compound of claim 21, or a pharmaceutically acceptable salt, or an N-oxide thereof, wherein Het is isothiazolyl.

27. A compound represented by

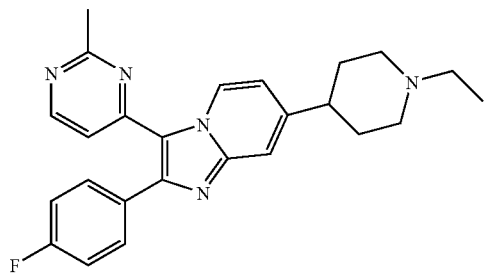

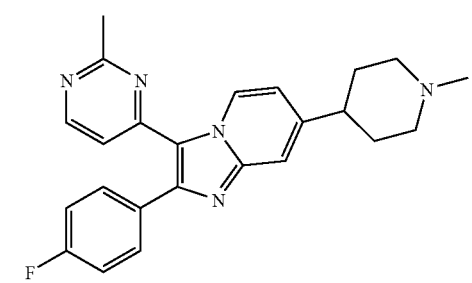

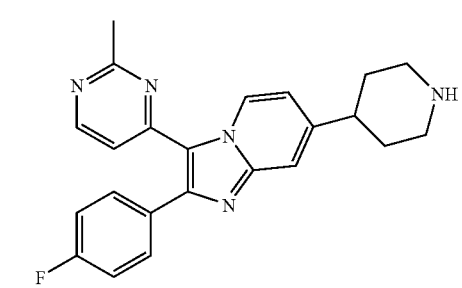

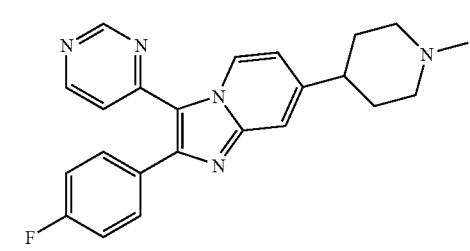

-continued

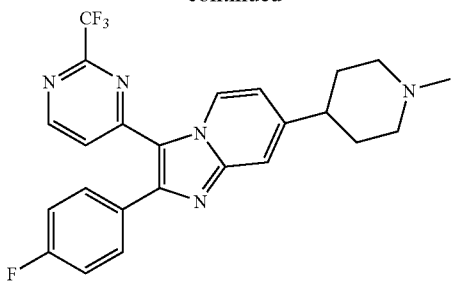

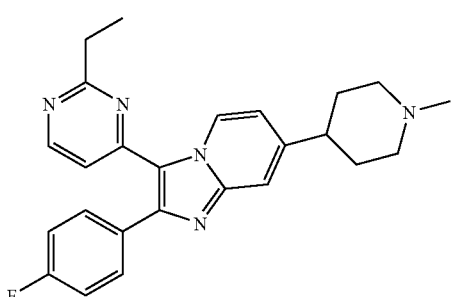

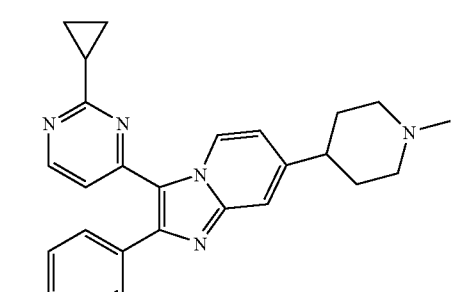

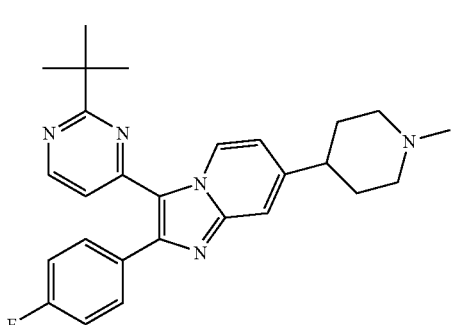

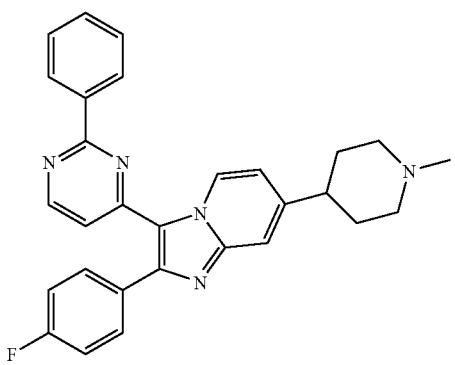

-continued

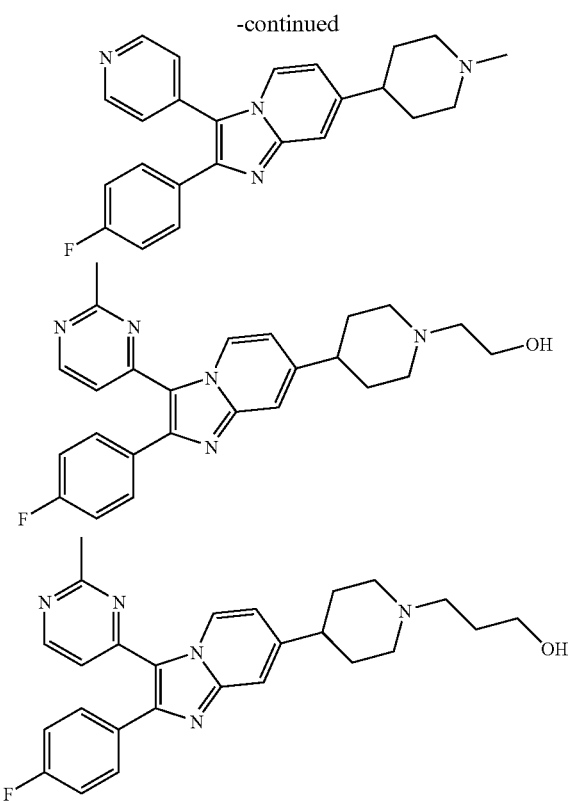

or a pharmaceutically acceptable salt, or an N-oxide thereof.

28. A method for controlling coccidiosis in poultry which comprises administering to said poultry a therapeutically effective amount, of a compound of claim 1.

29. A composition which comprises a compound of claim 1 and a pharmaceutically acceptable carrier.

30. The composition of claim 29 further comprising a second anticoccidial agent.

31. The composition of claim 30 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

32. The composition of claim 30 wherein said second anticoccidial agent is selected from the group consisting of amprolium, ethopabate, lasalocid, monensin, salinomycin, and diclazuril.

33. The composition of claim 29 wherein said carrier is poultry feedstuff.

34. The composition of claim 33 further comprising a second coccidial agent.

35. The composition of claim 34 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

36. The composition of claim 34 wherein said second anticoccidial agent is selected from the group consisting of amprolium, ethopabate, lasalocid, monensin, salinomycin, and diclazuril.

37. The composition of claim 29 wherein said carrier is poultry feed premix.

38. The composition of claim 37 further comprising a second anticoccidial agent.

39. The composition of claim 38 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

40. A composition of claim 38 wherein said second anticoccidial agent is selected from the group consisting of amprolium, ethopabate, lasalocid, monensin, salinomycin, and diclazuril.

41. A method for controlling malaria in a mammalian patient which comprises administering to said patient a therapeutically effective amount, of the compound of claim 1.

42. A method for controlling African trypanosomiasis in a mammalian patient which comprises administering to said patient a therapeutically effective amount, of a compound of claim 1.

43. A method for controlling Chagas disease in a mammalian patient which comprises administering to said patient a therapeutically effective amount, of a compound of claim 1.

44. A method for controlling toxoplasmosis in a mammalian patient which comprises administering to said patient a therapeutically effective amount, of a compound of claim 1.

45. A method for controlling coccidiosis in poultry which comprises administering to said poultry a therapeutically effective amount, of a compound of claim 21.

46. A method for controlling coccidiosis in poultry which comprises administering to said poultry a therapeutically effective amount, of a combination of anticoccidial agents comprising a compound of claim 21 and a second anticoccidial agent.

* * * * *